(12) United States Patent
McHenry et al.

(10) Patent No.: US 8,821,041 B2
(45) Date of Patent: Sep. 2, 2014

(54) FIBER OPTIC LIGHT SUPPLY SYSTEM AND CONNECTOR

(75) Inventors: Marguerite McHenry, Redwood City, CA (US); Daniel Bass, Half Moon Bay, CA (US); Terry Johnston, Redwood City, CA (US)

(73) Assignee: Tedan Surgical Innovations, LLC., Sugarland, TX (US)

( * ) Notice: Subject to any disclaimer, the term of this patent is extended or adjusted under 35 U.S.C. 154(b) by 211 days.

(21) Appl. No.: 13/538,367

(22) Filed: Jun. 29, 2012

(65) Prior Publication Data

US 2014/0003084 A1 Jan. 2, 2014

(51) Int. Cl.
*G02B 6/36* (2006.01)
(52) U.S. Cl.
USPC .................. 385/92; 385/53; 385/88; 385/89; 385/90
(58) Field of Classification Search
CPC .. G02B 6/4292; G02B 6/4246; G02B 6/4201; G02B 6/42; G02B 6/36
USPC .............. 385/53, 88, 89, 90, 91, 92
See application file for complete search history.

(56) References Cited

U.S. PATENT DOCUMENTS 6,357,933 B1 * 3/2002 Bradley et al. .............. 385/81
6,705,765 B2 * 3/2004 Lampert et al. ............. 385/77

FOREIGN PATENT DOCUMENTS

JP 08-94879 * 4/1996

OTHER PUBLICATIONS

Endoscopic Cable Replacements | CUDA, http://www.cuda.com/products-page/endoscopic-cables/endoscopic-cable-replacements (2011).

* cited by examiner

*Primary Examiner* — Jennifer Doan
(74) *Attorney, Agent, or Firm* — Kramer Amado P.C.

(57) ABSTRACT

A connector for connecting a fiber optic cable to a light source comprising a female adaptor having a receiving bore and a channel projecting into the receiving bore; a male ferrule, having a first portion insertable into at least part of the receiving bore, and a second portion defined at least partially by a tapered diameter region; and a compressible ring member disposed in the channel that engages the tapered portion when the male ferrule is inserted in the female adaptor in order to provide some resistance to removal of the male ferrule from the female adaptor.

20 Claims, 4 Drawing Sheets

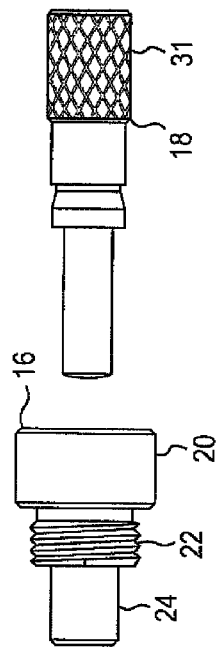
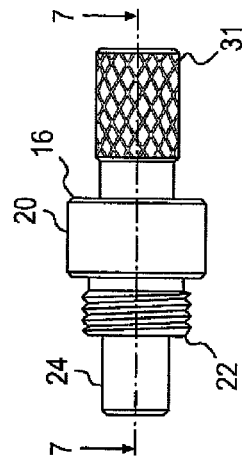
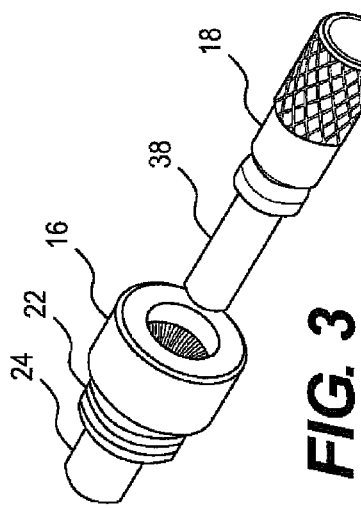
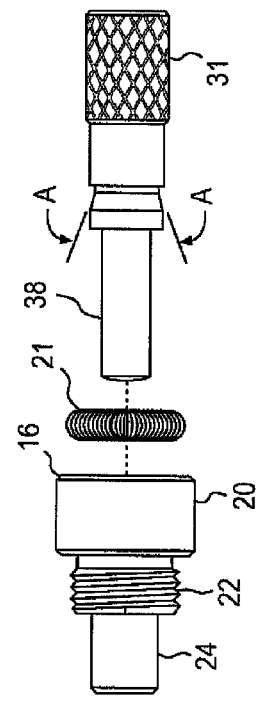
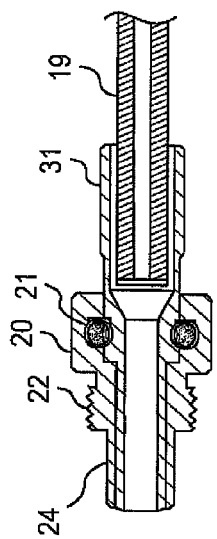
FIG. 3
FIG. 4
FIG. 5
FIG. 6
FIG. 7

FIBER OPTIC LIGHT SUPPLY SYSTEM AND CONNECTOR

FIELD OF THE INVENTION

Some embodiments of the invention pertain to the field of fiber optic illumination. For example, some embodiments of the invention relate to the transmission of light via fiber optic cables to provide illumination of a worksite such as a physician's surgical worksite. Further, some embodiments of the invention relate to connectors used to connect fiber optic cables to a light source.

BACKGROUND OF THE INVENTION

Fiber optic light transmission is in wide use in industry. In some cases, the purpose of the light transmission is simply to provide visible illumination onto a work surface, such as a surgical area. In some cases, fiber optic transmission lines may be routed near retractors or attached to a retractor or instrument, or other surgical equipment in order to provide illumination of the part of the body being worked on, as well as the equipment in proximity of the area. Fiber optic cables for this purpose themselves are well known, and have a transmission end which shines the light onto the surface. The receiving end of such a cable is typically connected to a light source such as an incandescent or LED light disposed within an enclosure. Various types of light sources that may be employed could include halogen, xenon, or high intensity discharge lights such as metal halide, high-pressure sodium, low-pressure sodium, and mercury vapor. It may be desirable to releasably connect the input end of a fiber optic cable to the output junction of the light source box.

SUMMARY OF THE INVENTION

In light of the present need for fiber optic light connectors, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

In another aspect some embodiments comprise a light source, as well as connector for connecting a fiber optic cable to a light source, comprising: a female adaptor having a receiving bore and a channel projecting into the receiving bore; a male ferrule, having a first portion insertable into at least part of the receiving bore, and a second portion defined at least partially by a tapered portion; and a compressible ring member disposed in the channel that engages the tapered portion when the male ferrule is inserted in the female adaptor in order to provide resistance to removal of the male ferrule from the female adaptor.

Other aspects of some embodiments include a connector for connecting a fiber optic cable to a light source comprising: a female adaptor having a connecting portion adapted to attach to the light source and having a receiving bore and a channel projecting into the receiving bore; a male ferrule having a receiving portion adapted to attach to the fiber optic cable and having a first portion with a first diameter insertable into at least part of the receiving bore, and a second portion at least partially having a second diameter less than the first diameter; and a compressible ring member disposed in the channel that engages the second portion when the male ferrule is inserted in the female adaptor in order to provide some resistance to removal of the male ferrule from the female adaptor.

BRIEF DESCRIPTION OF THE DRAWINGS

FIG. 3 is a partially exploded perspective view of a connector assembly.

FIG. 4 is a side partially exploded view of the connector of FIG. 3.

FIG. 5 is a more completely exploded side view of the connector of FIG. 3.

FIG. 6 is a side view of the connector of FIG. 3 in a connected condition.

FIG. 7 is a cross-sectional view taken through lines 7-7 in FIG. 6, also showing the fiber optic cable.

DETAILED DESCRIPTION

Figure 1:
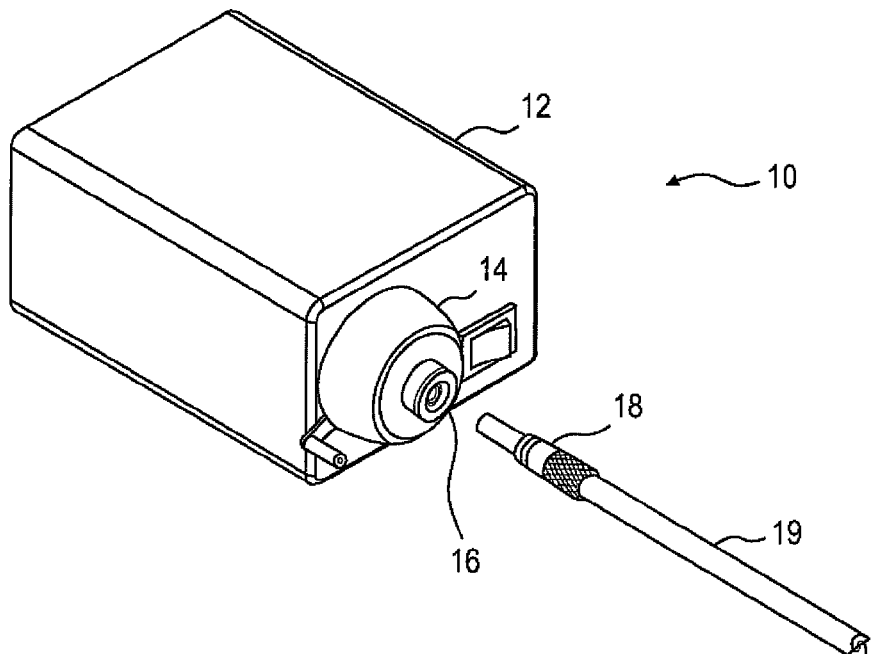
FIG. 1 is a perspective view showing a light source box having a fiber optic cable disconnected.

Various preferred embodiments of the invention will now be described as examples, with reference to the drawing figures, in which like reference numerals refer to like parts throughout.

Figure 2:
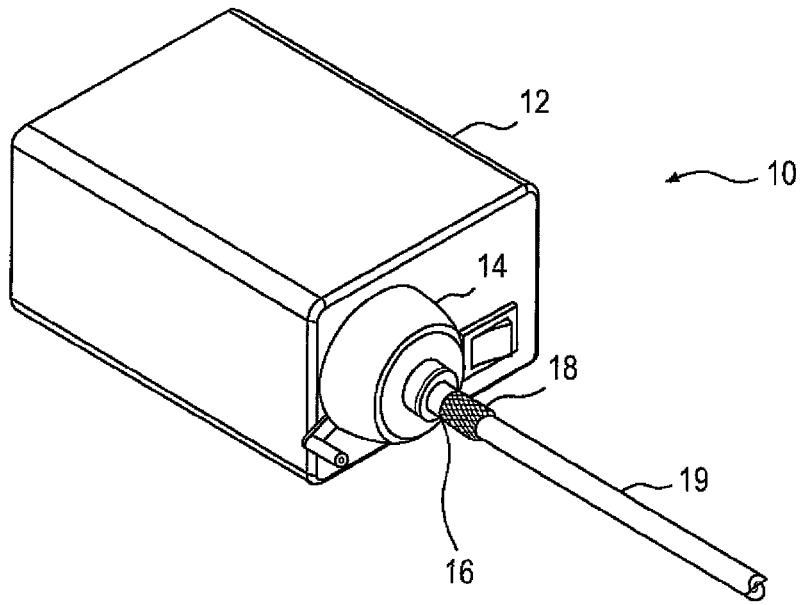
FIG. 2 is a perspective view similar to FIG. 1 showing the fiber optic cable connected to the light source box.

FIGS. 1 and 2 illustrate an embodiment of an entire light providing system 10. System 10 includes a light source box 12, which is a general housing having a light source (not shown) therein. The light source box 12, however, can be considered as a single entire component which projects light out of a light outlet port 14. The light outlet port 14 is associated with an illumination source such as an incandescent bulb or LED to provide light through an aperture in the center of the output port 14.

A female adaptor 16 has a threaded portion so that it may be threadably engaged into a light output aperture of the light output port 14. The female adaptor 16 has a bore through its center so that light is transmitted into and through the central bore (see FIG. 9) of the female adaptor 16.

A male ferrule 18 is affixed to the end of a fiber optic cable 20 and can be generally inserted into the bore 40 of the female adaptor 16, as will be described in more detail below, and as shown in more detail in drawing FIGS. 3-10.

FIG. 2 shows the system 10 in an operative condition with the male ferrule 18 inserted into the female adaptor 16, such that light from the light supply box 12 is provided into the fiber optic cable 20. This light can be transmitted through the cable length to be outputted from a distal end of the fiber optic cable which is not shown. The distal end of the fiber optic cable 20 may be directed at a work area in order to illuminate the work area.

Figure 8:
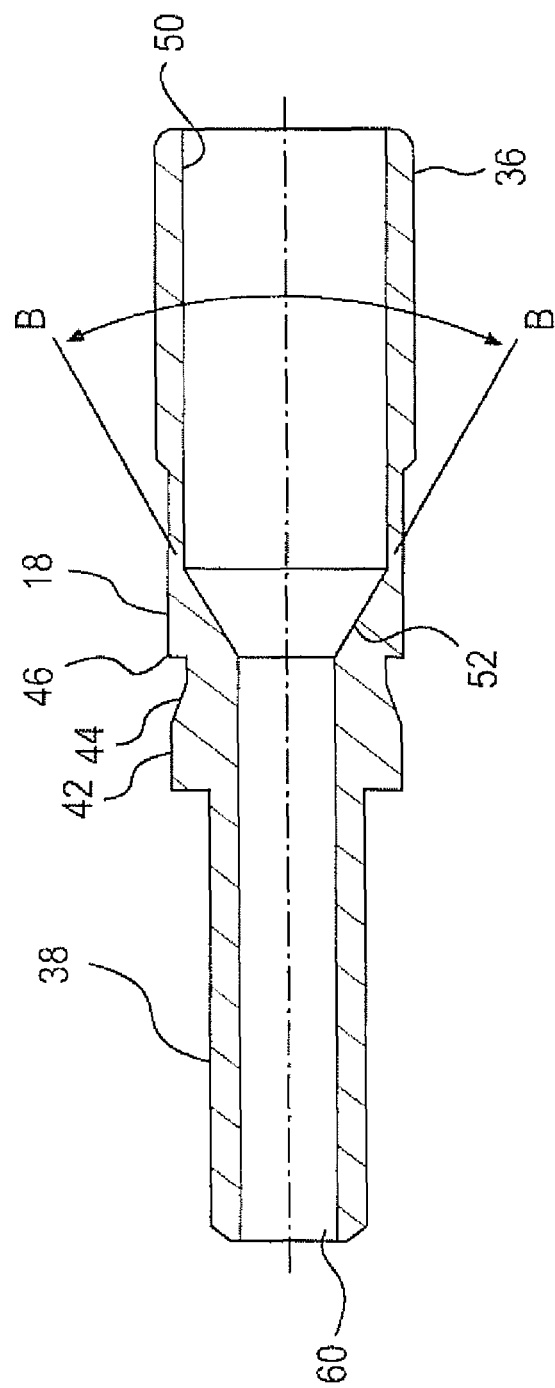
FIG. 8 is a cross-sectional view taken similar to FIG. 7, but showing only a male ferrule component of the connector.
Figure 10:
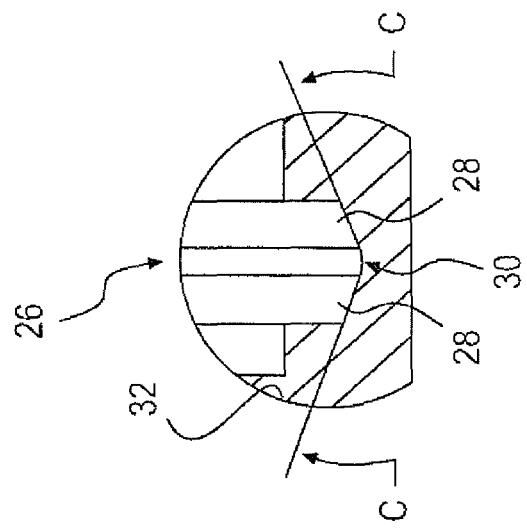
FIG. 10 is a cross-sectional detail view of the area labeled E in FIG. 9.
Figure 9:
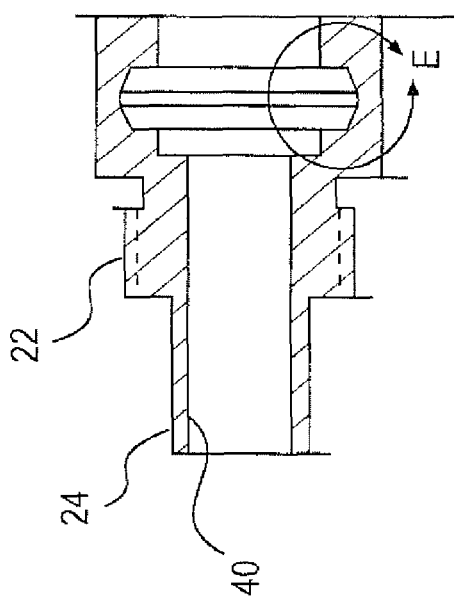
FIG. 9 is a cross-sectional view similar to FIG. 7, but showing only a female adaptor portion of the assembly.

FIGS. 3-10 illustrate additional details of the connection of the female adaptor 16 with the male ferrule 18. FIG. 5 illustrates a spring 21 which is discussed in more detail below. The spring 21 is in general a ring shaped compressible element. In this preferred embodiment, the spring 21, which is also known as a C-spring, is a toroidal coil spring that is thus deformable to some degree in the radial direction. The spring 21 may be made of many materials, but preferably will be a coiled metal such as steel. In other embodiments, a rubber or other elastomeric ring having the same or a similar overall ring shape may be used. However, in certain embodiments, a metallic material may be preferred for the spring 21. The female adaptor 16 includes a main body portion 20 and a threaded portion. The threaded portion engages with corresponding threads at the light transmission opening of the light projecting housing 14. The female adaptor may also have a smaller diameter projecting portion 24 which could fit into a complimentary bore in the light source housing 16. Further, as can be seen in FIGS. 7, 9 and 10, the female adaptor 16 has a channel 26 disposed in the internal bore thereof. The channel 26 may be of any suitable shape adapted to receive the spring 21, while permitting some deflection of the internal diameter of the spring 21. In the illustrated preferred embodiment, the channel 26 is formed by two opposed double sections 28 which may be joined by a radius area 30. In such a configuration, the angle C may preferably be approximately 135°, and the radius angle of area 30 may be selected as is convenient for manufacturing purposes. The female adaptor 16 also has an internal shoulder 32 which acts against a stop for the degree of insertion of the male ferrule 18.

Returning to FIGS. 4-9 and particularly to FIGS. 7 and 8, the male ferrule 18 may have a knurled end 36. Such a knurled end 36 is provided to facilitate grip of the male ferrule 18.

The male ferrule 18 also has a projecting portion 38 which is sized to fit into a complimentary bore 40 in the female adaptor 16. The male ferrule 18 also has a flange portion 42 leading to a tapered portion 44 and a shoulder 46. As the male ferrule 18 is inserted into the female adaptor 16, the extension 38 will pass through the open region defined by the spring 21 and will begin to slide into the bore 40. The tapered portion 44 has at least partially a diameter that is less than the diameter of the flange 42. As insertion is continued, the spring will ride over the flange 42, being compressed in the process. Further insertion of the male ferrule 18 will cause the spring to ride over the tapered portion 44 thus expanding somewhat and providing a frictional interlock of the male ferrule 18 inside the female adaptor 16. This configuration is shown in FIG. 7. It will be appreciated that the stop 32 of the female adaptor 16 is engaged with the stop surface 46 of the male ferrule thus limiting any further forward travel. On the other hand, a predetermined fictional force is required to remove the male ferrule 18, by a force exerted between the slightly compressed spring 21 and its contact with the tapered portion 44. In this way, a snug but releasable connection is provided, which in most embodiments will not leak any significant amount of light outside of the box 12.

FIG. 7 shows a fiber optic cable 20 inserted into the larger diameter bore 50 of the male ferrule 18 as shown in FIG. 8. The fiber optic cable illustrated in FIG. 7 can be any suitable well known or future developed fiber optic cable typically having a central core that is transmissive of light, and an outer sheath that may be opaque to light. The bore 50 that receives the fiber optic cable may lead to a tapered internal bore region 52 which may have an included angle B of approximately 60°. The tapered portion 52 leads to a smaller diameter bore 60 which is an open bore that simply receives light from the light emission source 12. The tapered region 44 may have an included angle A of approximately 32.6° (as shown in FIG. 5).

The female adaptor 16 and male ferrule 18 may be made of any suitable material. In some preferred embodiments they may be made of stainless steel.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A connector for connecting a fiber optic cable to a light source, comprising:
   a female adaptor having a receiving bore and a channel projecting into the receiving bore;
   a male ferrule, having a first portion insertable into at least part of the receiving bore, and a second portion defined at least partially by a tapered portion, wherein the tapered portion provides an opposing surface that reduces in diameter while tapering from a distal end defined by a flange, to a proximal end defined by a shoulder; and
   a compressible ring member disposed in the channel that engages the tapered portion when the male ferrule is inserted in the female adaptor in order to provide opposing resistance to removal of the male ferrule from the female adaptor.

2. The connector according to claim 1, wherein the compressible ring member is a toroidal coil metal spring.

3. The connector according to claim 1, wherein the female adaptor has a threaded portion that is threadably engageable into a light source.

4. The connector according to claim 1, wherein the tapered portion of the male ferrule is tapered at an angle of approximately 32.6°.

5. The connector according to claim 1, wherein the male ferrule has a first end adapted to project into a receiving bore in the female adaptor, and a second end having a second bore adapted to receive a fiber optic cable.

6. A light source apparatus, comprising:
   a fiber optic cable;
   a light source;
      a female adaptor for connection to the light source, and having a receiving bore and a channel projecting into the receiving bore;
      a male ferrule for connection to the fiber optic cable, and having a first portion positioned at a distal end defined by a flange, the first portion being insertable into at least part of the receiving bore, and a second portion positioned at a proximal end defined by a shoulder and defined at least partially by a tapered portion, wherein the tapered portion provides an opposing surface that reduces in diameter while tapering from the distal end to the proximal end; and
      a compressible ring member disposed in the channel that engages the tapered portion when the male ferrule is inserted in the female adaptor in order to provide resistance to removal of the male ferrule from the female adaptor.

7. The apparatus according to claim 6, wherein the compressible ring member is a toroidal coil metal spring.

8. The apparatus according to claim 6, wherein the female adaptor has a threaded portion that is threadably engageable into the light source.

9. The apparatus according to claim 6, wherein the tapered portion of the male ferrule is tapered at an angle of approximately 32.6°.

10. The apparatus according to claim 6, wherein the male ferrule has a first end adapted to project into a receiving bore in the female adaptor, and a second end having a second bore adapted to receive the fiber optic cable.

11. The apparatus according to claim 10, wherein the second bore is attached to the fiber optic cable.

12. A connector for connecting a fiber optic cable to a light source comprising:
- a female adaptor having a connecting portion adapted to attach to the light source and having a receiving bore and a channel projecting into the receiving bore;
- a male ferrule having a receiving portion adapted to attach to the fiber optic cable and having a first portion positioned at a distal end defined by a flange, the first portion having a first diameter insertable into at least part of the receiving bore, and a second portion positioned at a proximal end defined by a shoulder, the second portion at least partially having a second diameter, less than the first diameter; and
- a compressible ring member disposed in the channel that engages the second portion when the male ferrule is inserted in the female adaptor in order to provide some resistance to removal of the male ferrule from the female adaptor.

13. The connector according to claim 12, wherein the compressible ring member is a toroidal coil metal spring.

14. The connector according to claim 12, wherein the female adaptor has a threaded portion that is threadably engageable into a light source.

15. The connector according to claim 12, wherein the second portion comprises a tapered portion of the male ferrule is tapered at an angle of approximately 32.6°.

16. The connector according to claim 12, wherein the male ferrule has a first end adapted to project into a receiving bore in the female adaptor, and a second end having a second bore adapted to receive the fiber optic cable.

17. A method for connecting a fiber optic cable to a light source, comprising:
- providing a female adaptor having a receiving bore and a channel projecting into the receiving bore;
- providing a male ferrule, having a first portion insertable into at least part of the receiving bore, and a second portion defined at least partially by a tapered portion, wherein the tapered portion provides an opposing surface that reduces in diameter while tapering from a distal end defined by a flange, to a proximal end, defined by a shoulder;
- providing a compressible ring member disposed in the channel that engages the tapered portion when the male ferrule is inserted in the female adaptor in order to provide opposing resistance to removal of the male ferrule from the female adaptor; and
- inserting the male ferrule into the female adapter to provide resistance to removal of the male ferrule from the female adaptor.

18. The method according to claim 17, wherein the compressible ring member is a toroidal coil metal spring.

19. The method according to claim 17, wherein the female adaptor has a threaded portion that is threadably engageable into the light source.

20. The method according to claim 17, wherein the male ferrule has a first end adapted to project into a receiving bore in the female adaptor, and a second end having a second bore adapted to receive the fiber optic cable.

* * * * *